US011559254B2

(12) United States Patent
Kim et al.

(10) Patent No.: US 11,559,254 B2
(45) Date of Patent: Jan. 24, 2023

(54) METHOD, SYSTEM AND NON-TRANSITORY COMPUTER-READABLE RECORDING MEDIUM FOR ASSESSMENT OF AUTOREGULATION PERFORMANCE BASED ON HEMODYNAMICS

(71) Applicant: OBE LAB., INC., Daejeon (KR)

(72) Inventors: Jae Myoung Kim, Daejeon (KR); Hyeon Min Bae, Daejeon (KR)

(73) Assignee: OBE LAB., INC., Daejeon (KR)

( * ) Notice: Subject to any disclaimer, the term of this patent is extended or adjusted under 35 U.S.C. 154(b) by 288 days.

(21) Appl. No.: 16/600,685

(22) Filed: Oct. 14, 2019

(65) Prior Publication Data
US 2021/0068749 A1    Mar. 11, 2021

(30) Foreign Application Priority Data
Sep. 5, 2019 (KR) .................. 10-2019-0110388

(51) Int. Cl.
*A61B 5/00* (2006.01)
*A61B 5/026* (2006.01)
*A61B 5/1455* (2006.01)

(52) U.S. Cl.
CPC .......... *A61B 5/4884* (2013.01); *A61B 5/0261* (2013.01); *A61B 5/14552* (2013.01); *A61B 5/6803* (2013.01); *A61B 5/7282* (2013.01)

(58) Field of Classification Search
CPC ... A61B 5/4884; A61B 5/0261; A61B 5/7282; A61B 5/6803; A61B 5/14552; A61B 5/14553; A61B 5/0075; A61B 5/4035; A61B 5/7239; A61B 5/7275; A61B 5/6814

See application file for complete search history.

(56) References Cited

U.S. PATENT DOCUMENTS

| 2011/0046491 A1* | 2/2011 | Diamond | A61B 5/14552 385/33 |
| 2011/0105912 A1* | 5/2011 | Widman | A61B 5/021 600/483 |
| 2013/0303874 A1* | 11/2013 | Diamond | A61B 5/0077 600/383 |

(Continued)

OTHER PUBLICATIONS

Jurgen A. H. R. Claassen, Benjamin D. Levine, and Rong Zhang "Dynamic cerebral autoregulation during repeated squat-stand maneuvers", Oct. 28, 2008, J App Physiol, 106, p. 153-160 (Year: 2008).*

(Continued)

*Primary Examiner* — Allen Porter
*Assistant Examiner* — Abid A Mustansir
(74) *Attorney, Agent, or Firm* — Dinsmore & Shohl LLP; Yongsok Choi, Esq.

(57) ABSTRACT

According to one aspect of the invention, there is provided a method for assessing blood flow regulation performance based on hemodynamics, comprising the steps of: calculating second biometric information corresponding to a time differential of first biometric information on a hemoglobin concentration measured from a cerebral part of a subject; and assessing blood flow regulation performance of the subject with reference to a response that occurs in the second biometric information in correspondence to a change in a posture of the subject.

7 Claims, 8 Drawing Sheets

(56) References Cited

U.S. PATENT DOCUMENTS

2017/0367650 A1* 12/2017 Wallois ............... A61B 5/0075

OTHER PUBLICATIONS

Jae-Myoung Kim, et al., "Assessment of Cerebral Autoregulation Using Continuous-Wave Near-Infrared Spectroscopy During Squat-Stand Maneuvers In Subjects With Symptoms of Orthostatic Intolerance", Online Article, URL: https://www.nature.com/articles/s41598-018-31685-y, Published Sep. 5, 2018.

* cited by examiner

METHOD, SYSTEM AND NON-TRANSITORY COMPUTER-READABLE RECORDING MEDIUM FOR ASSESSMENT OF AUTOREGULATION PERFORMANCE BASED ON HEMODYNAMICS

CROSS-REFERENCE TO RELATED APPLICATION(S)

This application claims priority to Korean Patent Application Serial No. 10-2019-0110388 filed on Sep. 5, 2019, the entire contents of which are hereby incorporated by reference.

STATEMENT REGARDING PRIOR DISCLOSURE BY THE INVENTOR OR A JOINT INVENTOR UNDER 37 C.F.R. § 1.77(b)(6)

Kim et al, Assessment of cerebral autoregulation using continuous-wave near-infrared spectroscopy during squat-stand maneuvers in subjects with symptoms of orthostatic intolerance (hereinafter "Kim reference"), was published on Sep. 5, 2018, which is 1 year or less before the effective filing date of the present application, Sep. 5, 2019. A copy of the Kim reference is provided on a concurrently filed Information Disclosure Statement pursuant to the guidance of 78 Fed. Reg. 11076 (Feb. 14, 2013). Co-authors Jae Myoung Kim and Hyeon Min Bae invented and conceived of the inventive subject matter disclosed in the Kim reference. Co-authors Jong-Kwan Choi, Mingyu Choi, Minsu Ji, Gunpil Hwang, and Sang-Bae Ko did not invent or conceive of any of the inventive subject matter captured in the Kim reference. These co-authors acted either in a support capacity or under instruction by Jae Myoung Kim and Hyeon Min Bae.

FIELD OF THE INVENTION

The present invention relates to a method, system and non-transitory computer-readable recording medium for assessment of blood flow regulation performance based on hemodynamics.

BACKGROUND

Autonomic nervous system disorders, which are caused by various factors such as diabetes, peripheral nerve diseases, aging, and Parkinson's disease, can cause uncomfortable symptoms such as a blood pressure drop upon standing (i.e., orthostatic hypotension), less sweating or dry eyes and mouth, and indigestion. As methods for testing autonomic nervous system disorders or abnormalities, a sweating test, Valsalva maneuver, electrocardiography, a head-up tilt test, and a pupillary response test have been introduced.

According to the test methods introduced so far, it is determined whether there is an autonomic nervous system disorder based on a result of measuring a change in blood pressure or pulse. However, it is difficult to accurately measure the change in blood pressure or pulse in real time, and the sensitivity of the change (i.e. the degree of change according to a stimulus) varies from person to person. Thus, there is a limitation that it is difficult to accurately and quickly determine whether a person has an autonomic nervous system disorder and how severe the autonomic nervous system disorder of the person is.

Meanwhile, near-infrared spectroscopy (NIRS) is a recently introduced method for indirectly analyzing the activity in a body part (e.g., a brain) of a person by measuring the degree of attenuation of near-infrared light (due to scattering and absorption by oxidized hemoglobin or non-oxidized hemoglobin) which varies with hemodynamic changes (e.g., changes in concentrations of oxyhemoglobin and deoxyhemoglobin) occurring in the body part. More specifically, when hemodynamic changes occurring in a brain is measured, for example, near-infrared light having a wavelength range of about 630 nm to 1300 nm may be transmitted through a skull of the person to the depth of about 1 cm to 3 cm from the skull. By irradiating such near-infrared light to a head part of the person and detecting near-infrared light reflected or scattered therefrom, it is possible to measure hemodynamic changes (e.g., a change in a concentration of blood oxygen (i.e., oxidized hemoglobin)) occurring in the cerebral cortex of the person.

More specifically, according to the near-infrared spectroscopy, the neural activity occurring in a human brain (particularly, a cortex) may be quantified by arranging near-infrared light irradiation or detection modules called optodes at predetermined intervals in various parts of a head of a person, and analyzing signals related to hemodynamics (e.g., optical density (OD) signals based on the near-infrared spectroscopy) acquired from the optodes.

In this connection, the inventor(s) present a novel and inventive technique for assessing the performance of autonomic nervous system regulation (specifically, cerebral blood flow regulation) of a subject based on hemodynamics that can be measured using near-infrared spectroscopy.

SUMMARY OF THE INVENTION

One object of the present invention is to solve all the above-described problems.

Another object of the invention is to provide a method, system and non-transitory computer-readable recording medium for accurately assessing blood flow regulation performance related to autonomic nervous system disorders in real time, by calculating second biometric information corresponding to a time differential of first biometric information on a hemoglobin concentration measured from a cerebral part of a subject; and assessing blood flow regulation performance of the subject with reference to a response that occurs in the second biometric information in correspondence to a change in a posture of the subject.

The representative configurations of the invention to achieve the above objects are described below.

According to one aspect of the invention, there is provided a method for assessing blood flow regulation performance based on hemodynamics, comprising the steps of: calculating second biometric information corresponding to a time differential of first biometric information on a hemoglobin concentration measured from a cerebral part of a subject; and assessing blood flow regulation performance of the subject with reference to a response that occurs in the second biometric information in correspondence to a change in a posture of the subject.

According to another aspect of the invention, there is provided a system for assessing blood flow regulation performance based on hemodynamics, comprising: a biometric information management unit configured to calculate second biometric information corresponding to a time differential of first biometric information on a hemoglobin concentration measured from a cerebral part of a subject; and an assessment management unit configured to assess blood flow regulation performance of the subject with reference to a response that occurs in the second biometric information in correspondence to a change in a posture of the subject.

In addition, there are further provided other methods and systems to implement the invention, as well as non-transitory computer-readable recording media having stored thereon computer programs for executing the methods.

According to the invention, it is possible to accurately assess the performance of autonomic nervous system regulation or blood flow regulation in real time based on hemodynamics measured by near-infrared spectroscopy.

According to the invention, it is possible to carry out the assessment using continuous biometric data specified based on signals measured in real time, thereby reducing the time required for the assessment as compared to an orthostatic hypotension test method based on conventional blood pressure measurement.

According to the invention, it is possible to determine not only a patient group having severe disorders but also a symptom group having mild symptoms, thereby improving the sensitivity and accuracy of the assessment as compared to an orthostatic hypotension test method based on conventional blood pressure measurement.

DETAILED DESCRIPTION

Figure 1A:
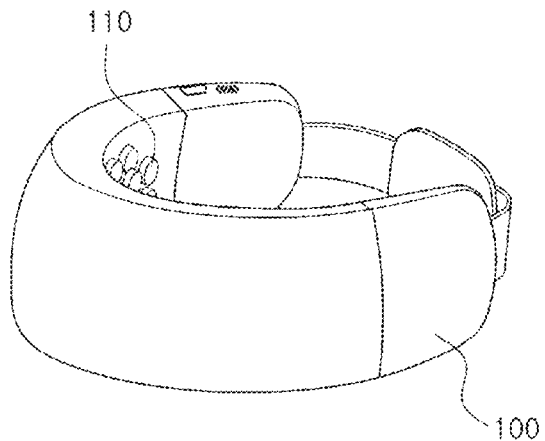
FIG. 1A schematically shows the external configuration of a device according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the positions or arrangements of individual elements within each of the disclosed embodiments may also be modified without departing from the spirit and scope of the invention. Therefore, the following detailed description is not to be taken in a limiting sense, and the scope of the invention, if properly described, is limited only by the appended claims together with all equivalents thereof. In the drawings, like reference numerals refer to the same or similar functions throughout the several views.

Hereinafter, preferred embodiments of the present invention will be described in detail with reference to the accompanying drawings to enable those skilled in the art to easily implement the invention.

Herein, hemodynamics to be measured by a device and an assessment system may include blood composition (e.g., oxyhemoglobin concentration, deoxyhemoglobin concentration, blood oxygen saturation, etc.), blood flow and blood volume.

Configuration of an Assessment System

Hereinafter, the internal configuration of a device and an assessment system crucial for implementing the invention and the functions of the respective components thereof will be discussed.

Figure 1B:
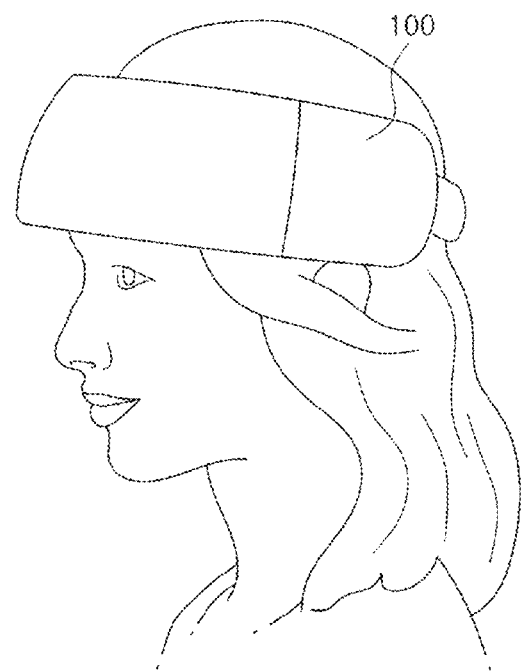
FIG. 1B schematically shows the external configuration of a device according to one embodiment of the invention.

FIGS. 1A and 1B schematically show the external configuration of a device according to one embodiment of the invention.

Referring to FIGS. 1A and 1B, a device 100 according to one embodiment of the invention may be worn on a body part (e.g., a head part) of a subject (see FIG. 1B), and may function to measure a signal from the subject. The measured signal is processed or analyzed as will be described below, so that it may be used in assessing the activity occurring in the body part of the subject (e.g., blood flow changes occurring in the cerebrum).

Specifically, the device 100 according to one embodiment of the invention may include a plurality of optodes 110 for irradiating near-infrared light to a head part of a subject and detecting near-infrared light reflected or scattered from the head part of the subject (more specifically, from the cerebral venous blood of the subject) (see FIG. 1A). For example, optical density (OD) signals based on near-infrared spectroscopy may be measured by the plurality of optodes 110 included in the device 100 according to one embodiment of the invention.

Figure 2:
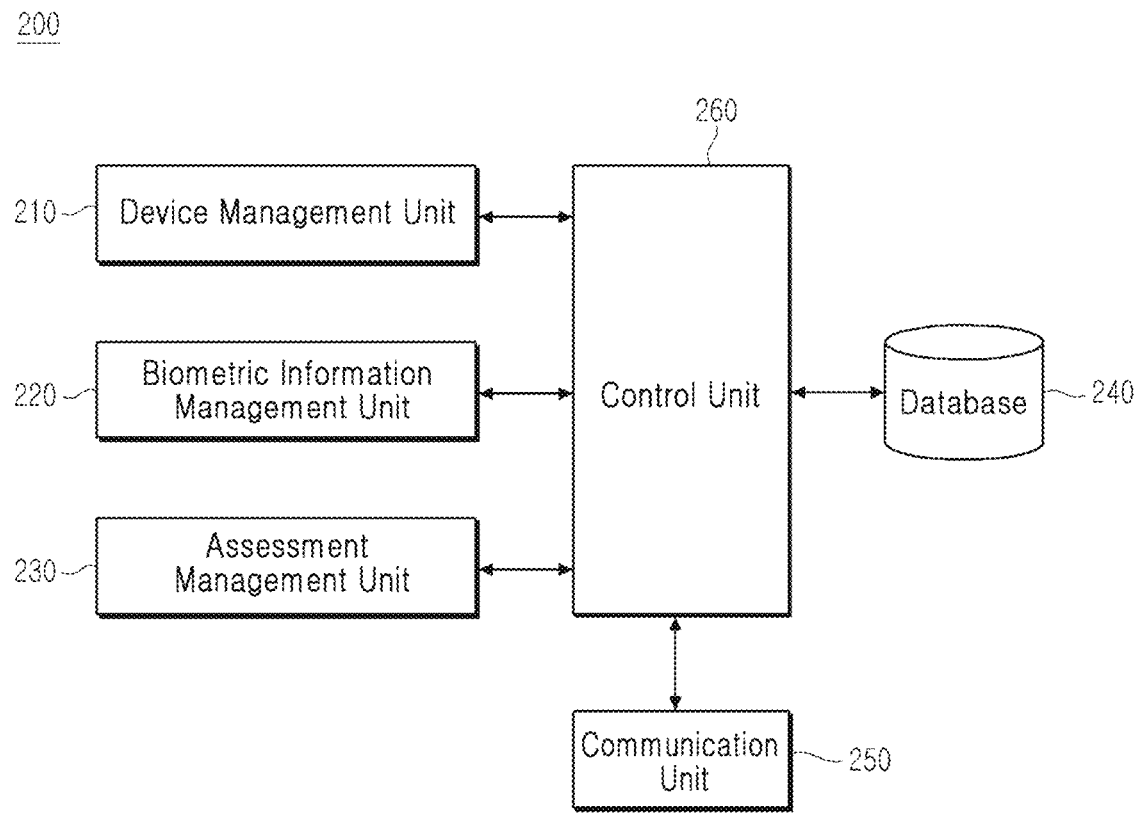
FIG. 2 illustratively shows the internal configuration of an assessment system according to one embodiment of the invention.

FIG. 2 illustratively shows the internal configuration of an assessment system according to one embodiment of the invention.

Referring to FIG. 2, an assessment system 200 according to one embodiment of the invention may comprise a device management unit 210, a biometric information management unit 220, an assessment management unit 230, a database 240, a communication unit 250, and a control unit 260. According to one embodiment of the invention, at least some of the device management unit 210, the biometric information management unit 220, the assessment management unit 230, the database 240, the communication unit 250, and the control unit 260 may be program modules to communicate with an external system (not shown). The program modules may be included in the assessment system 200 in the form of operating systems, application program modules and other program modules, while they may be physically stored in a variety of commonly known storage devices. Further, the program modules may also be stored in a remote storage device that may communicate with the assessment system 200. Meanwhile, such program modules may include, but not limited to, routines, subroutines, programs, objects, components, data structures, and the like for performing specific tasks or executing specific abstract data types as will be described below in accordance with the invention.

Meanwhile, although the assessment system 200 has been described as above, the above description is illustrative, and it will be apparent to those skilled in the art that at least a part of the components or functions of the assessment system 200 may be implemented or included in the device 100 (which is a portable device worn on a body part of a subject), as necessary. Further, in some cases, all the functions and components of the assessment system 200 may be implemented or included in the device 100.

First, according to one embodiment of the invention, the device management unit 210 may function to manage the device 100 such that the plurality of optodes 110 included in the device 100 may irradiate near-infrared light to a body part (e.g., a head part) of a subject and detect near-infrared light reflected or scattered from the body part of the subject. Further, the device management unit 210 according to one embodiment of the invention may manage other functions or components of the device 100 which are required to measure a biometric signal related to hemodynamics of the subject.

More specifically, according to one embodiment of the invention, the subject may change his/her posture by squatting for a predetermined time with the device 100 according to invention being worn on the head part of the subject, and then abruptly standing up. In this case, the device 100 according to one embodiment of the invention may measure a biometric signal related to hemodynamics of the head part (specifically, the cerebral part) of the subject while the posture of the subject changes. Here, according to one embodiment of the invention, the device 100 may measure an optical density (OD) signal by detecting near-infrared light reflected or scattered from the cerebral part of the subject using the plurality of optodes, and the optical density signal may be used in calculating a hemoglobin concentration as will be describe below.

Typically, when the subject changes his/her posture by squatting for a predetermined time and then abruptly standing up, blood pressure in the cerebral part of the subject drops rapidly because the subject's venous blood rushes to the lower limbs due to gravity. In order to compensate for the drop in the blood pressure, the subject's autonomic nervous system reacts to restore the blood pressure in the cerebral part to the previous state (or rest state). Accordingly, cerebral blood volume (CBV) and cerebral blood flow (CBF) of the subject change rapidly repeating increase and decrease.

The assessment system 200 according to one embodiment of the invention may assess whether autonomic nervous system regulation or blood flow regulation of the subject is normally performed, by estimating and analyzing the above cerebral hemodynamic changes based on hemodynamics (specifically, hemoglobin concentration) that can be measured using near-infrared spectroscopy.

Next, according to one embodiment of the invention, the biometric information management unit 220 may function to calculate first biometric information on a hemoglobin concentration measured from the cerebral part of the subject, and calculate second biometric information corresponding to a time differential of the hemoglobin concentration.

Specifically, the biometric information management unit 220 according to one embodiment of the invention may calculate the first biometric information from a total hemoglobin concentration (HbT) obtained by summing a oxyhemoglobin concentration ($HbO_2$) and a deoxyhemoglobin concentration (HbR) of the blood in the cerebral part of the subject, based on a result of detecting near-infrared light reflected or scattered from the cerebral part of the subject. For example, the first biometric information may be a relative value ($\Delta HbT$) corresponding to a difference between a baseline value and a hemoglobin concentration measured from the cerebral part of the subject.

Further, the biometric information management unit 220 according to one embodiment of the invention may calculate the second biometric information from a time differential (DHBT) of the total hemoglobin concentration calculated as the first biometric information. For example, the second biometric information may be a time differential ($d(\Delta HbT)/dt$) of the relative value corresponding to the difference between the baseline value and the hemoglobin concentration measured from the cerebral part of the subject.

According to one embodiment of the invention, the first biometric information (i.e., the total hemoglobin concentration) corresponds to the cerebral blood volume (CBV) of the subject and may change under the influence of measurement conditions or physical characteristics, and the second biometric information (i.e., the time differential of the total hemoglobin concentration) corresponds to the variation over time of the cerebral blood flow (CBF) and is not influenced by the measurement conditions or physical characteristics. Thus, the second biometric information (i.e., the time differential of the total hemoglobin concentration) may be an indicator that may be commonly used in assessing the performance of autonomic nervous system regulation or blood flow regulation of various subjects. The assessment system 200 according to one embodiment of the invention may accurately assess the performance of autonomic nervous system regulation or blood flow regulation of the subject based on the time differential of the total hemoglobin concentration.

Figure 3A:
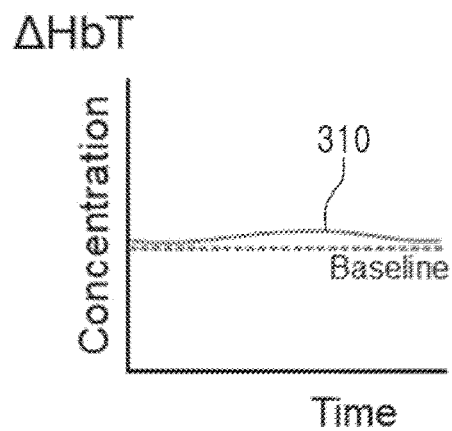
FIG. 3A illustratively shows a response that may occur in biometric information on hemoglobin concentration as a posture of a subject changes according to one embodiment of the invention.
Figure 3B:
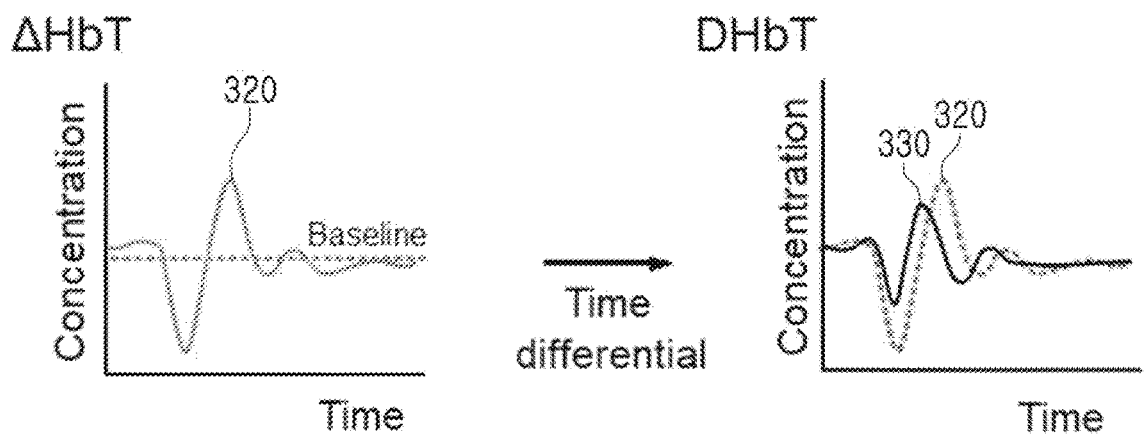
FIG. 3B illustratively shows a response that may occur in biometric information on hemoglobin concentration as a posture of a subject changes according to one embodiment of the invention.

FIGS. 3A and 3B illustratively show a response that may occur in biometric information on hemoglobin concentration as a posture of a subject changes according to one embodiment of the invention.

First, referring to FIG. 3A, when the subject is squatting still (i.e., when there is no change in the posture of the subject), a total hemoglobin concentration 310 of a cerebral part of the subject may not change significantly.

Next, referring to FIG. 3B, when the subject abruptly stands up after squatting still (i.e., when the posture of the subject changes rapidly), a total hemoglobin concentration 320 of the cerebral part of the subject may fluctuate rapidly in a manner that it increases significantly and then decreases significantly, and thus a time differential 330 of the total hemoglobin concentration may also change significantly.

Figure 4:
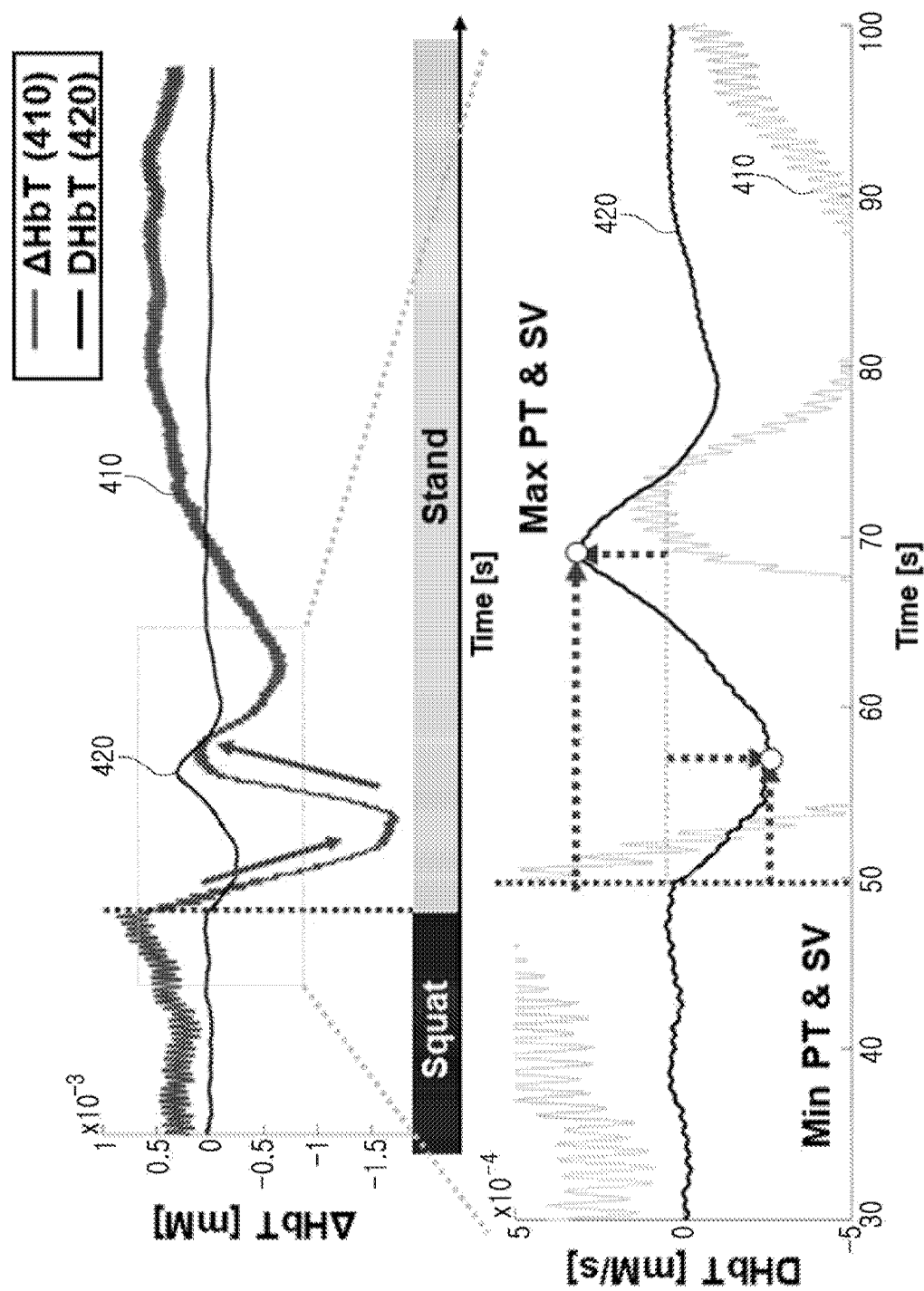
FIG. 4 illustratively shows a relationship between a hemoglobin concentration and a time differential of the hemoglobin concentration according to one embodiment of the invention.

FIG. 4 illustratively shows a relationship between a hemoglobin concentration and a time differential of the hemoglobin concentration according to one embodiment of the invention.

Referring to FIG. 4, while a hemoglobin concentration of a cerebral part of a subject fluctuates rapidly repeating decrease and increase as a posture of the subject changes, a time differential 420 of a total hemoglobin concentration 410 is the smallest when the slope is the smallest in the graph of the total hemoglobin concentration 410 (see "Min PT & SV" in FIG. 4), and conversely, the time differential 420 of the total hemoglobin concentration 410 is the largest when the slope is the largest in the graph of the total hemoglobin concentration 410 (see "Max PT & SV" in FIG. 4).

Next, according to one embodiment of the invention, the assessment management unit 230 may function to assess blood flow regulation performance of the subject with reference to a response that occurs in a time differential of a total hemoglobin concentration in correspondence to a change in a posture of the subject. Further, in the course of the above assessment, the assessment management unit 230 according to one embodiment of the invention may estimate a change in blood flow according to the change in the posture of the subject, with reference to the response that occurs in the time differential of the total hemoglobin concentration.

Specifically, according to one embodiment of the invention, the assessment management unit 230 may assess the blood flow regulation performance of the subject with reference to at least one characteristic parameter that appears in the time differential of the total hemoglobin concentration. For example, when the blood flow regulation performance of the subject is assessed, at least one of a maximum value of the differential (i.e., Max SV), a minimum value of the differential (i.e., Min SV), a time point when the maximum value of the differential appears (i.e., Max PT), and a time point when the minimum value of the differential appears (i.e., Min PT) may be referred to as the characteristic parameter.

Further, according to one embodiment of the invention, the assessment management unit 230 may assess the blood flow regulation performance of the subject may assess the performance of autonomic nervous system regulation or blood flow regulation of the subject, by comparing the response that occurs in the time differential of the total hemoglobin concentration of the subject with a pattern of a response that occurs in a time differential of a total hemoglobin concentration of at least one subject group.

Figure 5A:
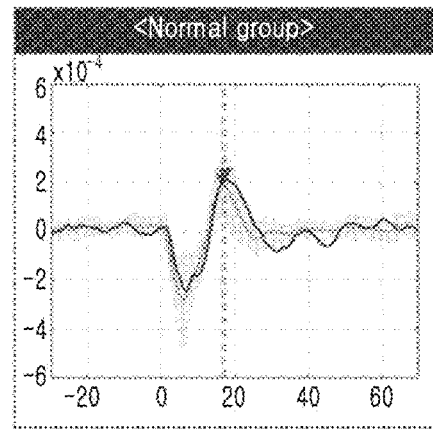
FIG. 5A illustratively shows a response that occurs in a time differential of a total hemoglobin concentration as a posture of a subject in each of a normal group, a symptom group and a patient group changes according to one embodiment of the invention.
Figure 5B:
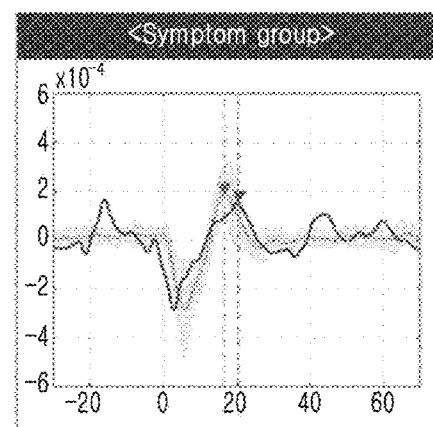
FIG. 5B illustratively shows a response that occurs in a time differential of a total hemoglobin concentration as a posture of a subject in each of a normal group, a symptom group and a patient group changes according to one embodiment of the invention.
Figure 5C:
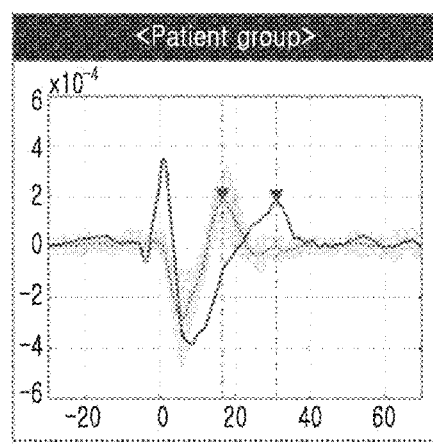
FIG. 5C illustratively shows a response that occurs in a time differential of a total hemoglobin concentration as a posture of a subject in each of a normal group, a symptom group and a patient group changes according to one embodiment of the invention.

FIGS. 5A to 5C illustratively show a response that occurs in a time differential of a total hemoglobin concentration as a posture of a subject in each of a normal group, a symptom group and a patient group changes according to one embodiment of the invention.

Referring to FIGS. 5A to 5C, when a normal range of a time differential of a total hemoglobin concentration (corresponding to the shaded area in FIGS. 5A to 5C) is specified from a plurality of measurement results for a plurality of subjects belonging to a normal group whose blood flow regulation performance is normal, a certain subject may be assessed to belong to the normal group when a time differential of a total hemoglobin concentration of the subject (corresponding to a line shown in darker color in FIG. 5A) does not deviate from the normal range (see FIG. 5A); a certain subject may be assessed to belong to the symptom group (i.e., to have symptoms but not being a patient) when a time differential of a total hemoglobin concentration of the subject (corresponding to a line shown in darker color in FIG. 5B) slightly deviates from the normal range (see FIG. 5B); and a certain subject may be assessed to belong to the patient group when a time differential of a total hemoglobin concentration of the subject (corresponding to a line shown in darker color in FIG. 5C) significantly deviates from the normal range (see FIG. 5C).

Figure 6:
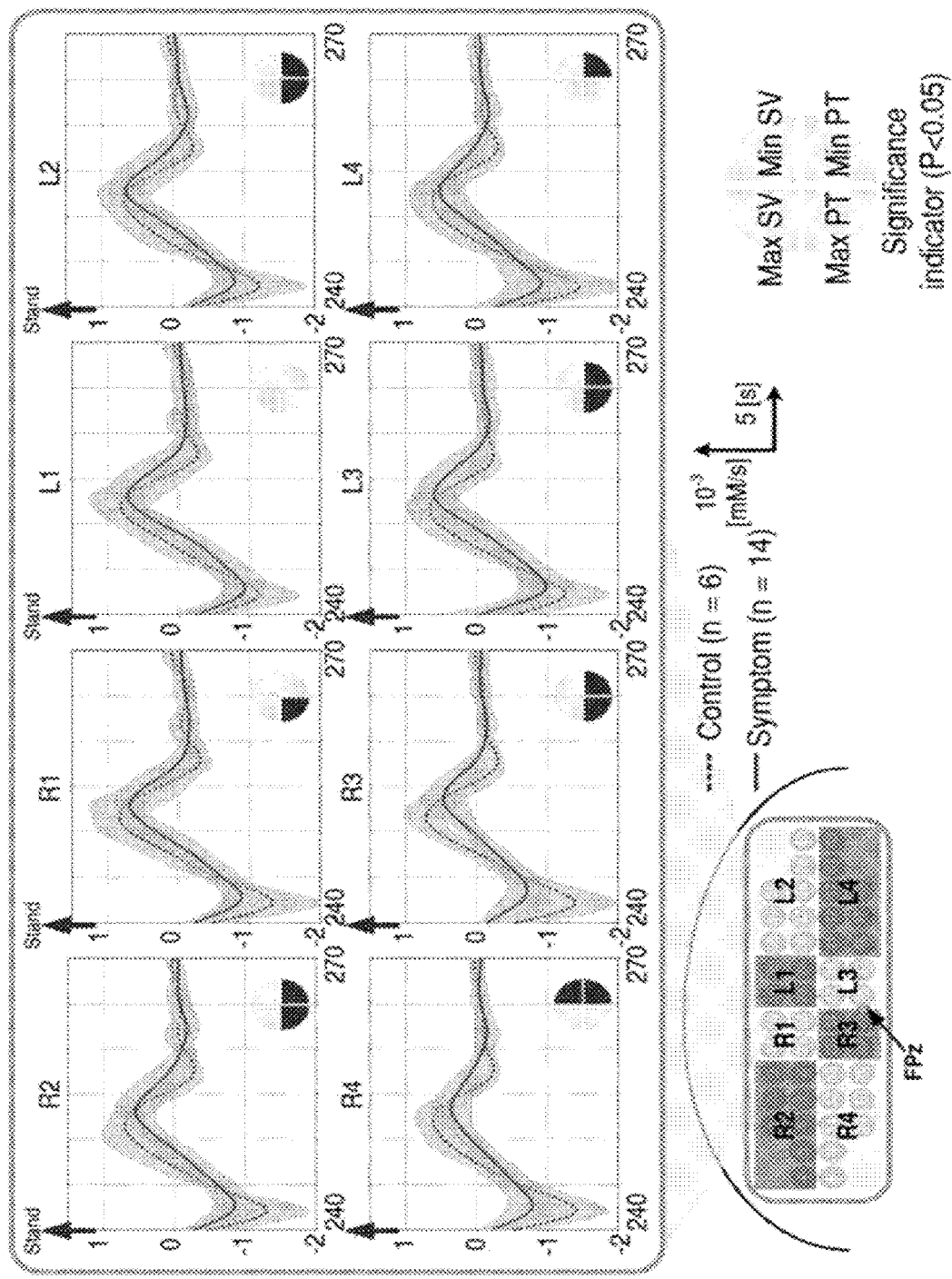
FIG. 6 illustratively shows a situation in which blood flow regulation performance of a subject is assessed by analyzing a response that occurs in a time differential of a total hemoglobin concentration according to one embodiment of the invention.

FIG. 6 illustratively shows a situation in which blood flow regulation performance of a subject is assessed by analyzing a response that occurs in a time differential of a total hemoglobin concentration according to one embodiment of the invention.

In the embodiment of FIG. 6, blood flow regulation performance was assessed for 6 subjects belonging to a normal group and 14 subjects belonging to a symptom group.

Referring to FIG. 6, it can be seen that in most of a plurality of optode areas L1 to L4 and R1 to R4 of the device 100, there is a significant difference between a response to a time differential of a total hemoglobin concentration of the normal group and a response to a time differential of a total hemoglobin concentration of the symptom group. For example, when a time differential of a total hemoglobin concentration calculated based on an optical density signal measured in the optode area R2 of the device 100 is compared, it can be seen that there is a significant difference between the normal group and symptom group in terms of a time point when the maximum value appears (i.e., Max PT) and a time point when the minimum value appears (i.e., Min PT).

Further, according to one embodiment of the invention, the assessment management unit 230 may express a result of assessing the performance of autonomic nervous system regulation or blood flow regulation of the subject as a quantitative indicator (e.g., a score), and may generate assessment result information including the quantitative indicator.

Figure 7:
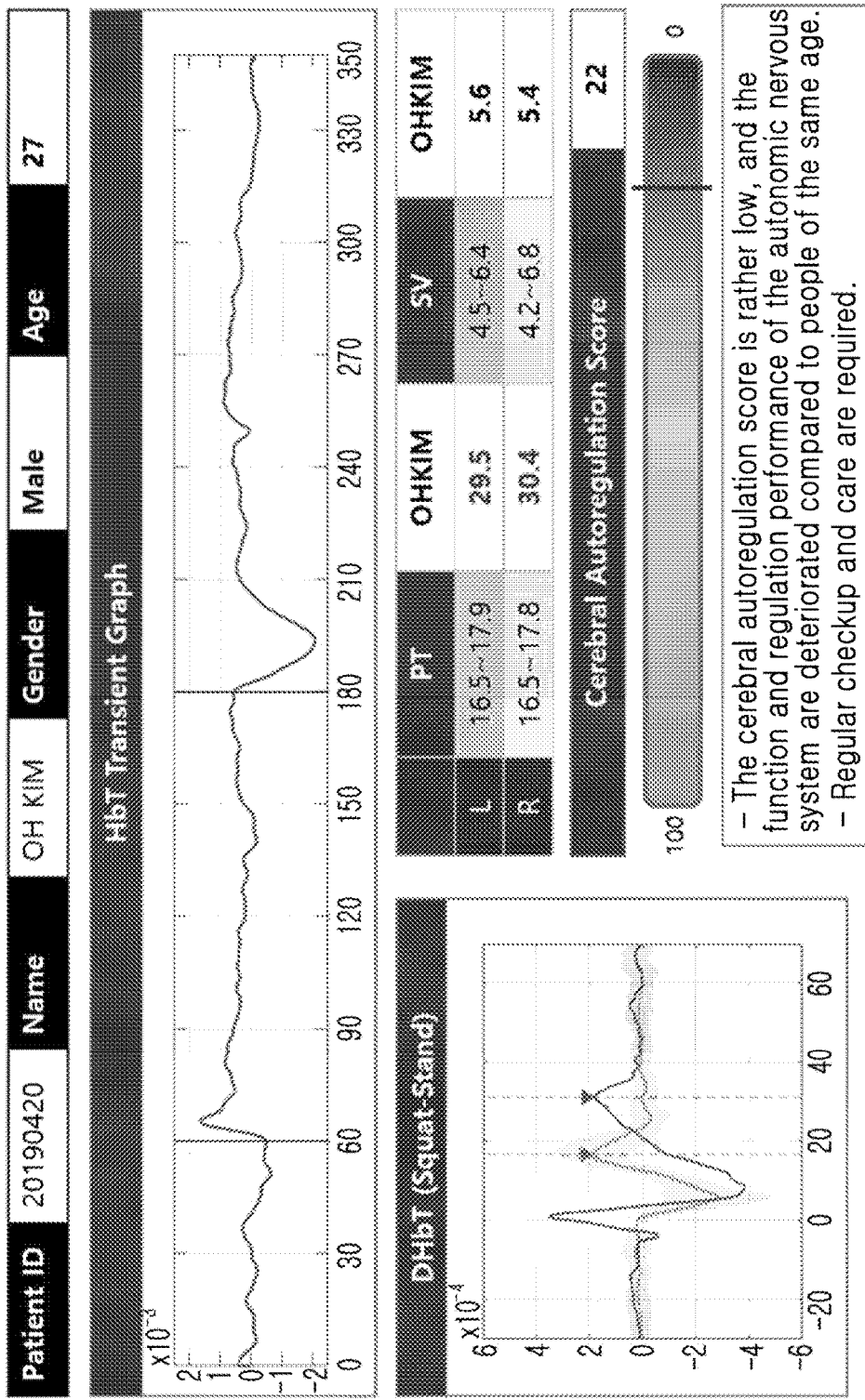
FIG. 7 illustratively shows information on a result of assessing blood flow regulation performance of a subject according to one embodiment of the invention.

FIG. 7 illustratively shows information on a result of assessing blood flow regulation performance of a subject according to one embodiment of the invention.

Referring to FIG. 7, there may be provided a graph for a total hemoglobin concentration of a subject, a graph for a time differential of the total hemoglobin concentration of the subject, information on differences from a normal group, a score for the performance of autonomic nervous system regulation (or blood flow regulation), and information on a commentary on the assessment result.

Figure 8A:
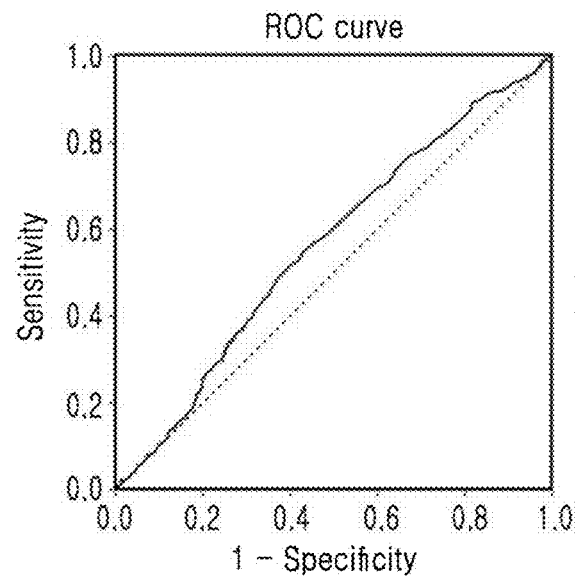
FIG. 8A illustratively shows a result of comparing the performance of an assessment method according to the prior art and an assessment method according to the invention.
Figure 8B:
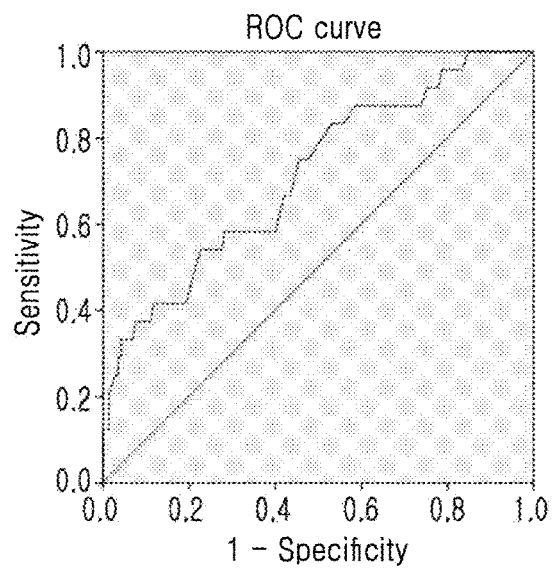
FIG. 8B illustratively shows a result of comparing the performance of an assessment method according to the prior art and an assessment method according to the invention.

FIGS. 8A and 8B illustratively show a result of comparing the performance of an assessment method according to the prior art and an assessment method according to the invention.

Referring to FIGS. 8A and 8B, a receiver operating characteristic (ROC) curve of a result of assessing blood flow regulation performance based on blood pressure according to the prior art showed an area under curve (AUC) of 0.564 (for a patient group of 94 persons and a normal group of 635 persons; 95% CI; see FIG. 8A), and a ROC curve of a result of assessing blood flow regulation performance based on near-infrared spectroscopy according to the invention showed an AUC of 0.714 (for a patient group of 24 persons and a normal group of 145 persons; 95% CI; see FIG. 8B). Therefore, it can be seen that the assessment method according to the invention has significantly better accuracy than the assessment method according to the prior art.

Further, according to the prior art in which blood flow regulation performance is assessed based on blood pressure, the time required for the assessment is long and the accuracy of the assessment is not high, because the assessment should be carried out based on discontinuous data acquired at time intervals corresponding to the time required for measuring blood pressure. However, according to the invention in which blood flow regulation performance is assessed based on near-infrared spectroscopy, there are advantages that the time required for the assessment is short and the accuracy of the assessment is high, because the assessment can be carried out based on continuous data on hemoglobin concentration acquired in real time.

However, it is noted that the detailed configurations related to the assessment method according to the invention are not necessarily limited to the above-described embodiments, and may be changed without limitation as long as the objects of the invention may be achieved.

Meanwhile, according to one embodiment of the invention, the database 240 may store a variety of information on an optical density signal, a hemoglobin concentration, a time differential of the hemoglobin concentration, and the like, which are measured or calculated from at least one subject. Further, according to one embodiment of the invention, the variety of information as above may be stored in the database 240 as grouped into at least one group (e.g., a normal group, a symptom group and a patient group). Although FIG. 2 shows that the database 240 is incorporated in the assessment system 200, the database 240 may be configured separately from the assessment system 200 as needed by those skilled in the art to implement the invention. Meanwhile, the database 240 according to the invention encompasses a computer-readable recording medium, and may refer not only to a database in a narrow sense but also to a database in a broad sense including file system-based data records and the like. The database 240 according to the invention may be even a collection of simple logs if one can search and retrieve data from the collection.

Meanwhile, the communication unit 250 according to one embodiment of the invention may function to enable the assessment system 200 to communicate with an external device.

Lastly, the control unit 260 according to one embodiment of the invention may function to control data flow among the device management unit 210, the biometric information management unit 220, the assessment management unit 230, the database 240, and the communication unit 250. That is, the control unit 260 may control inbound data flow or data flow among the respective components of the assessment system 200, such that the device management unit 210, the biometric information management unit 220, the assessment management unit 230, the database 240, and the communication unit 250 may carry out their particular functions, respectively.

Although the cases where a measurement signal used in calculating biometric information on hemodynamics is an optical density signal based on near-infrared spectroscopy have been mainly described above, the measurement signal is not necessarily limited thereto, and it is noted that any other type of measurement signal may be assumed as long as the objects or effects of the methods, systems, and non-transitory computer-readable recording media described herein may be achieved.

Further, although the cases where a body part to be measured and assessed is a head part (i.e., a brain) have been mainly described above, the body part to be measured and assessed according to the invention is not necessarily limited thereto, and it is noted that any other body part that can be measured and assessed based on hemodynamics may be assumed to be the body part to be measured and assessed according to the invention.

The embodiments according to the invention as described above may be implemented in the form of program instructions that can be executed by various computer components, and may be stored on a non-transitory computer-readable recording medium. The non-transitory computer-readable recording medium may include program instructions, data files, data structures and the like, separately or in combination. The program instructions stored on the non-transitory computer-readable recording medium may be specially designed and configured for the present invention, or may also be known and available to those skilled in the computer software field. Examples of the non-transitory computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be configured to operate as one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method for assessing blood flow regulation performance based on hemodynamics,
comprising the steps of:
irradiating, by a plurality of optodes embedded in a wearable head band, light to a cerebral part of a subject;
calculating, by a controller embedded in the wearable head band, a hemoglobin concentration based on the light reflected or scattered from the cerebral part of the subject;
calculating, by the controller, second biometric information corresponding to a time differential of first biometric information on the hemoglobin concentration, the first biometric information being a relative value corresponding to a difference between a baseline value and a total hemoglobin concentration of the hemoglobin concentration and the second biometric information being a time differential of the relative value; and assessing, by the controller, blood flow regulation performance of the subject with reference to a pattern of the second biometric information changed in response to a change in a posture of the subject, wherein in the assessing step, the blood flow regulation performance of the subject is assessed by comparing the pattern of the second biometric information of the subject with a pattern of the second biometric information of at least one subject group, and wherein the plurality of optodes are directed to the cerebral part of the subject when the wearable head band is worn by the subject.

2. The method of claim 1, wherein the first biometric information and the second biometric information are specified based on near-infrared light detected from the cerebral part of the subject using near-infrared spectroscopy (NIRS).

3. The method of claim 1, wherein in the assessing step, the blood flow regulation performance of the subject is assessed with reference to at least one of a maximum value of the time differential of the relative value, a minimum value of the time differential of the relative value, a time point when the maximum value of the time differential of the relative value appears, and a time point when the minimum value of the time differential of the relative value appears.

4. The method of claim 1, wherein in the assessing step, the posture of the subject changes from a squatting posture to a standing posture.

5. The method of claim 1, wherein in the assessing step, a change in blood flow according to the change in the posture of the subject is estimated with reference to the second biometric information changed in response to the change in the posture of the subject.

6. A non-transitory computer-readable recording medium having stored thereon a computer program for executing the method of claim 1.

7. A system for assessing blood flow regulation performance based on hemodynamics, comprising:

a wearable head band;

a plurality of optodes embedded in the wearable head band and configured to irradiate light to a cerebral part of a subject; and a controller embedded in the wearable head band and programmed to:

calculate a hemoglobin concentration based on the light reflected or scattered from the cerebral part of the subject;

calculate second biometric information corresponding to a time differential of first biometric information on the hemoglobin concentration, the first biometric information being a relative value corresponding to a difference between a baseline value and a total hemoglobin concentration of the hemoglobin concentration and the second biometric information being a time differential of the relative value;

assess blood flow regulation performance of the subject with reference to a pattern of the second biometric information changed in response to a change in a posture of the subject; and assess the blood flow regulation performance of the subject by comparing the pattern of the second biometric information of the subject with a pattern of the second biometric information of at least one subject group, wherein the plurality of optodes are directed to the cerebral part of the subject when the wearable head band is worn by the subject.

* * * * *